United States Patent
Sosnowski et al.

(10) Patent No.: US 6,984,986 B2
(45) Date of Patent: Jan. 10, 2006

(54) SITU FLUID CONDITION MONITORING

(75) Inventors: David R. Sosnowski, Lake Orion, MI (US); Gordon M. Fincannon, West Bloomfield, MI (US)

(73) Assignee: Eaton Corporation, Cleveland, OH (US)

( * ) Notice: Subject to any disclaimer, the term of this patent is extended or adjusted under 35 U.S.C. 154(b) by 9 days.

(21) Appl. No.: 10/786,818

(22) Filed: Feb. 24, 2004

(65) Prior Publication Data

US 2005/0184734 A1    Aug. 25, 2005

(51) Int. Cl.
  *G01N 27/06*   (2006.01)
  *G01R 27/08*   (2006.01)
  *G01R 23/16*   (2006.01)

(52) U.S. Cl. .................... 324/444; 324/698; 324/76.22

(58) Field of Classification Search ................ 324/698, 324/663, 444, 441, 76.77, 76.12, 76.13, 76.22, 324/553

See application file for complete search history.

(56) References Cited

U.S. PATENT DOCUMENTS

| 5,489,849 | A | 2/1996 | Sadoway |
| 6,278,281 | B1 | 8/2001 | Bauer et al. ................. 324/441 |
| 6,844,745 | B1 * | 1/2005 | Schachameyer et al. .... 324/698 |
| 6,861,851 | B2 * | 3/2005 | Lvovich et al. ............. 324/698 |
| 2002/0125899 | A1 | 9/2002 | Lvovich |
| 2003/0222658 | A1 | 12/2003 | Phillips |
| 2004/0085080 | A1 * | 5/2004 | Schilowitz et al. ......... 324/698 |
| 2004/0239344 | A1 * | 12/2004 | Hu .............................. 324/698 |
| 2005/0017738 | A1 * | 1/2005 | Lin et al. ..................... 324/698 |

FOREIGN PATENT DOCUMENTS

WO    WO 03/104798 A1    12/2003

OTHER PUBLICATIONS

PCT International Search report dated May 18, 2005, Application No. PCT/1B2005/000409.

* cited by examiner

*Primary Examiner*—Anjan Deb
(74) *Attorney, Agent, or Firm*—Anna M. Shih; Roger A. Johnston

(57) ABSTRACT

A database is compiled of values of the frequency $f_{NM}$ corresponding to the minimum reactance $Z''_{MIN}$ (Nyquist minimum) versus temperature $T_L$ over a selected range of temperatures for a probe immersed in a sample of the fluid to be monitored and excited by an a.c. voltage and the frequency swept over a range to cover both bulk fluid and electrode interface impedance characteristics. The probe is then excited in situ and the temperature measured. The Nyquist minimum is then determined from the database and the current measured on the low frequency (interfacial) side of the Nyquist minimum. The angle Θ of the rate of change of resistance Z″ with respect to resistance Z′ and magnitude of the impedance $Z_S$ is then determined from the current measurement; and, the fluid condition Ψ determined from a previously compiled database of values of Ψ, $Z_S$ and Θ.

4 Claims, 4 Drawing Sheets

SITU FLUID CONDITION MONITORING

BACKGROUND OF THE INVENTION

The present invention relates to real time monitoring of the condition of a fluid, such as engine lubricant during engine operation, by impedance spectroscopy wherein electrodes are immersed in the lubricant and excited with a relatively low voltage alternating current at frequencies indicative of the bulk impedance of the fluid and separately at frequencies indicative of the electrode surface properties. The use of impedance spectroscopy for fluid condition monitoring by the aforesaid method is known and described in U.S. Pat. No. 6,278,281 issued to Bauer, et al., assigned to the assignee of the present application.

The method of determining the condition of a fluid, and particularly lubricants, described in the aforesaid patent is subject to shifting as the temperature of the fluid varies in service and can introduce significant errors to the analysis of the probe signal. Heretofore, temperature compensation of the current measurements in order to provide an accurate indication of the bulk and electrode surface impedance, has proven difficult and therefore the determination of the impedance of the fluid rendered suspect with wide variations in the temperature during operation.

It has been desired to provide a way or means for determining the condition of a fluid by impedance spectroscopy derived from current measurements of a probe excited with an alternating current voltage in a manner which provides accurate correction the effects of temperature variation in the fluid and additionally provides sufficient resolution to yield a correct correlation of the fluid condition with values of impedance for known fluid conditions.

BRIEF SUMMARY OF THE INVENTION

The present invention provides a unique and novel technique for determining the condition of a fluid in situ by impedance spectroscopy with a probe inserted in the fluid and excited by an alternating current voltage with the change in impedance determine by current and phase angle measurements taken over a frequency sweep sufficient to include frequencies at which the current is sensitive separately to bulk fluid impedance and electrode/fluid interface impedance. A Nyquist plot is employed to determined the minimum reactance (Z") and the corresponding frequency; and, values of this "Nyquist minimum" are determined at temperature intervals over a range of operating temperatures. A database is then compiled of values of the temperature ($T_L$) and the corresponding Nyquist minimum frequency ($f_{NM}$) for use in subsequent in situ measurements.

With the Nyquist minimum frequency $f_{NM}$ determined at the measured fluid temperature, a frequency is selected a desired interval less than $f_{NM}$. The probe is then excited in situ at the selected frequency and current and phase angle measurements taken from which the magnitude of the impedance change $\Delta Z$ with reference to the Nyquist minimum is determined; and, the rate of change $\Theta$ of the reactance with respect to the resistance is determined. A fluid condition $\Psi$ is then determined by interpolation from a database previously and separately compiled for values of $\Delta Z$, $\Theta$ for known fluid conditions $\Psi$.

DETAILED DESCRIPTION OF THE INVENTION

Figure 1:
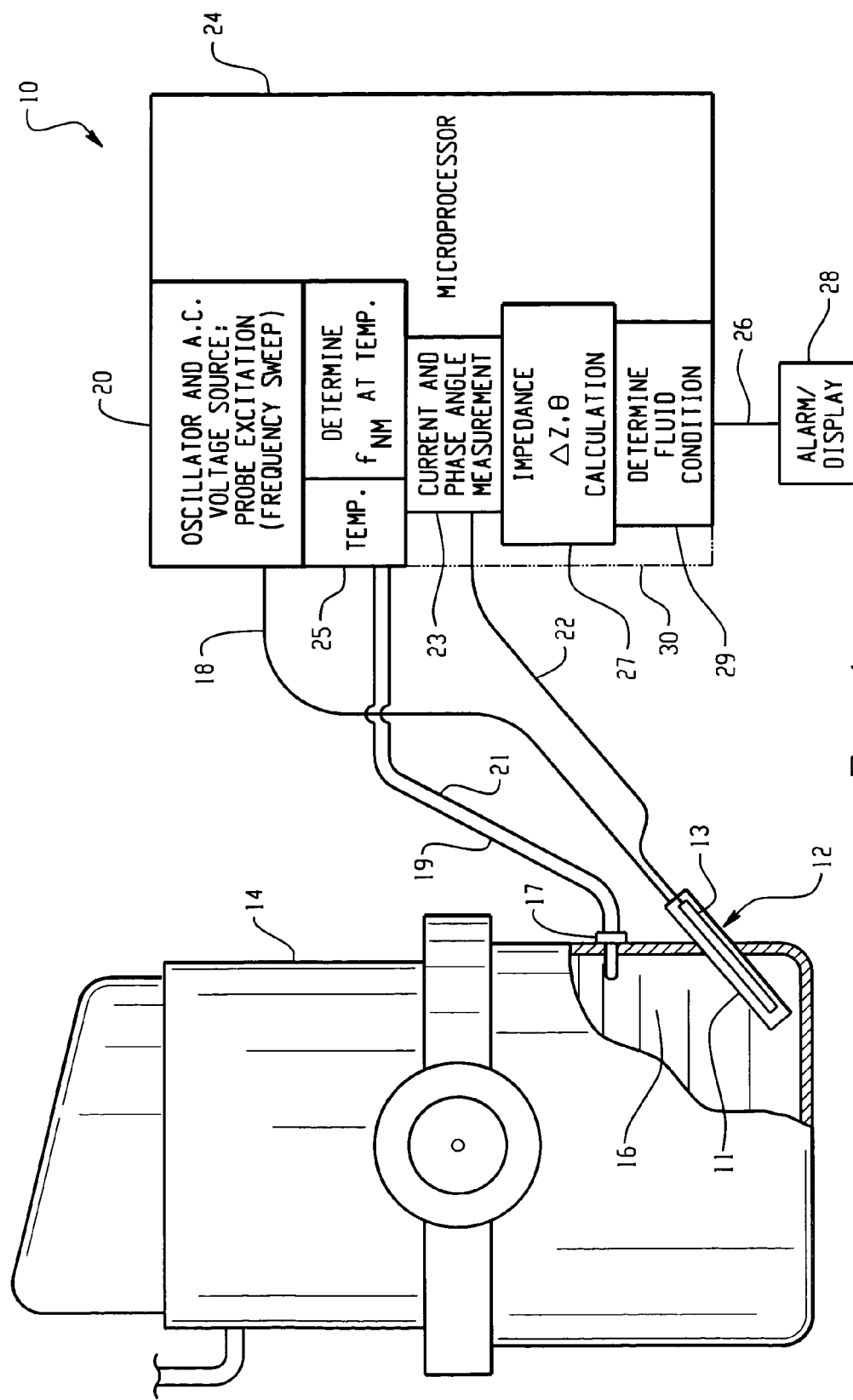
FIG. 1 is an embodiment of the invention for determining the in situ the condition of engine lubricant during operation.

Referring to FIG. 1, the system embodying the present invention is indicated generally at 10 and includes an impedance probe indicated generally at 12 inserted in through the crankcase of an engine 14 for monitoring the engine lubricant 16. The probe 12 includes an excitation electrode 11 connected by a lead 18 to voltage source 20 and pickup or measurement electrode 13 connected by lead 20 to a current and phase angle measurement section 23 connected to a microprocessor 24 in a controller 30.

A separate temperature sensor 17 is installed in the engine crankcase and is connected via leads 19, 21 to a temperature and frequency measuring section 25 of the controller 30. Controller 30 has an output 26 which provides a signal to an alarm/display unit 28 located remotely from controller 30.

The current and phase angle measurements taken in section 23 provide information to impedance calculation section 27 which in turn provides inputs to section 29 which determines the fluid condition from a database by interpolation as will hereinafter be described.

Figure 2:
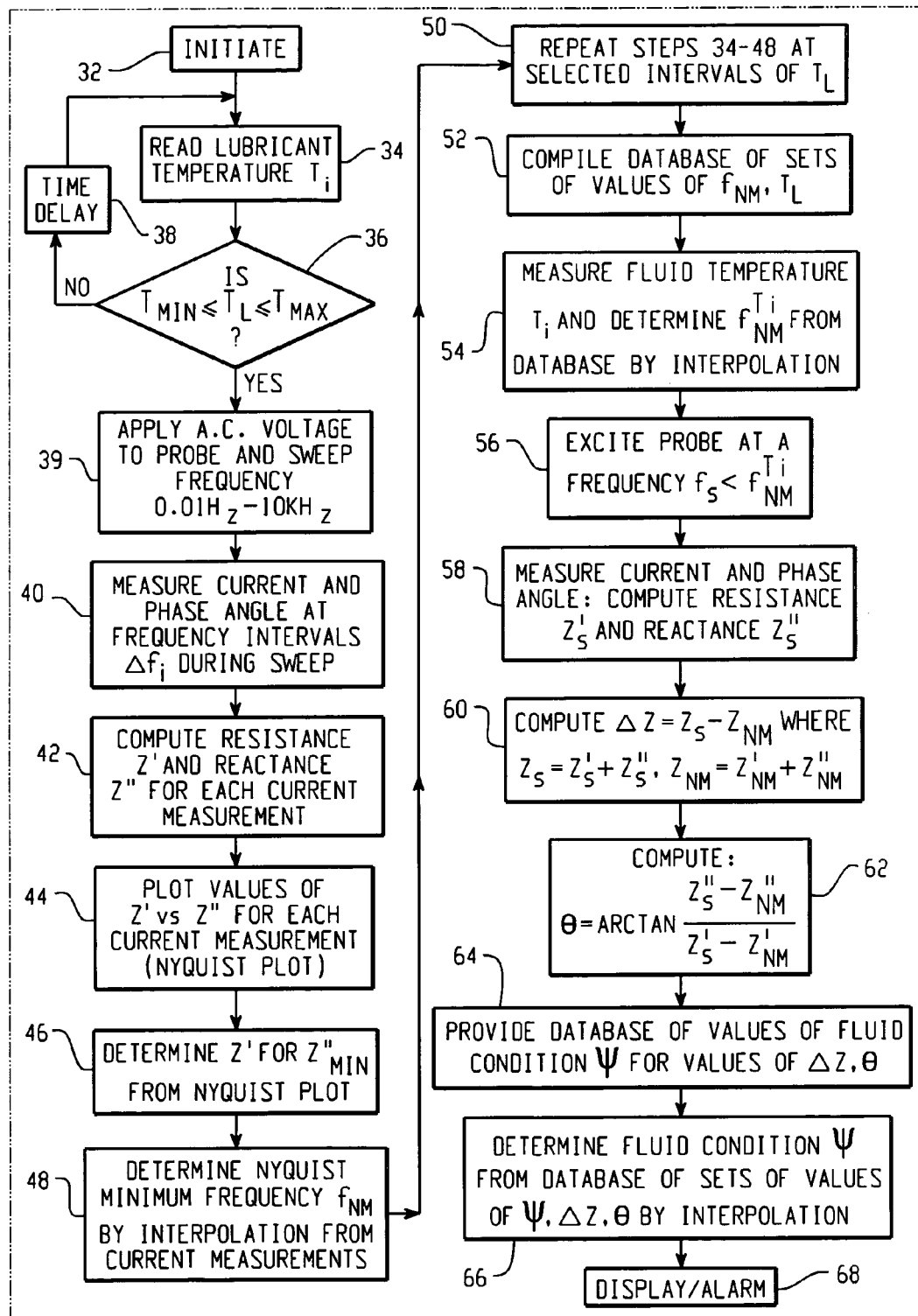
FIG. 2 is a block diagram of the system operation of FIG. 1.

Referring to FIG. 2, the operation of the system is shown in the form of a block diagram where the system is initiated at step 32 and reads the lubricant temperature from the sensor 17 at step 34. The system then proceeds to step 36 and makes a determination as to whether or not the fluid temperature $T_L$ is within desired limits $T_{MIN}$, $T_{MAX}$; and, if the determination at step 36 is negative, the system proceeds to step 38 and activates a time delay before returning to step 32. However, if the determination at step 36 is affirmative, the system proceeds to step 39 and begins to build a temperature compensation database for later in situ use and applies an a.c. voltage to the probe electrode 11 along line 18 and sweeps the frequency through a desired range. In the presently preferred practice of the invention, the frequency sweep is over the range at about 0.01 Hz to 10 kHz.

The system then proceeds to step 40, measures the current and the phase angle of the current at selected frequency intervals $\Delta f_i$.

The system then proceeds to step 42 and computes the resistance Z' and reactance Z" for each of the current measurements made in step 40. At step 44, values of Z' are plotted as a function of Z" for each of the current measurements in the well known format of a Nyquist plot. Samples of such plots are given in FIGS. 3a and 3b.

The system then proceeds to step 46 and determines the minimum reactance $Z"_{MIN}$ and the corresponding value of Z' from the Nyquist plot, e.g., "Nyquist minimum". The system then proceeds to step 48 and determines by interpolation from the current measurements the frequency $f_{NM}$ corresponding to the Nyquist minimum. The system then proceeds to step 50 and repeats steps 34 through 48 at selected intervals of the temperature $T_L$ and then proceeds to step 52 to compile a database of sets of values of $f_{NM}$ and $T_L$ which may be stored for later use. It will be understood that steps 34–52 may, if desired, be performed remotely from the engine in a sample of the lubricant to establish the temperature compensation database of step 52.

For in situ measurement, the system then proceeds to step 54 and measures the fluid temperature $T_i$ and determines the corresponding Nyquist minimum frequency $$f_{NM}^{T_i}$$

by interpolation from the database compiled in step 52.

The system then proceeds to step 56 where a frequency $f_S$ is chosen less than the Nyquist minimum $$f_{NM}^{T_i}$$

determined in step 54 and the probe is excited at the frequency $f_S$.

The system proceeds to step 58 where the current and phase angle of the excitation of step 56 are measured and the resistance $Z'_S$ and reactance $Z\Delta_S$ are computed from the measurements.

The system then proceeds to step 60 and computes the difference in impedance $\Delta Z = Z_S - Z_{NM}$ where $$Z_S = \left| \vec{Z'_S} + \vec{Z''_S} \right|$$

and $$Z_{NM} = \left| \vec{Z'_{NM}} + \vec{Z''_{NM}} \right|.$$

The system then proceeds to step 62 and computes the angle of the slope or the rate change of reactance with respect to impedance expressed as $$\Theta \arctan Z_{S''} - Z_{NM''} \frac{Z''_S - Z''_{NM}}{Z'_S - Z'_{NM}}.$$

The system then proceeds to step 64 where a database of values of known fluid condition $\Psi$ of values of $\Delta Z$ and $\Theta$ as previously determined is provided. The system then proceeds to step 68 and determines the actual fluid condition $\Psi$ by interpolation of the sets of values of $\Psi$, $\Delta Z$, $\Theta$ in the database provided in step 64.

The system then provides at step 68 a display of $\Psi$ or activates an alarm if $\Psi$ is less outside a predetermined range.

Figure 3A:
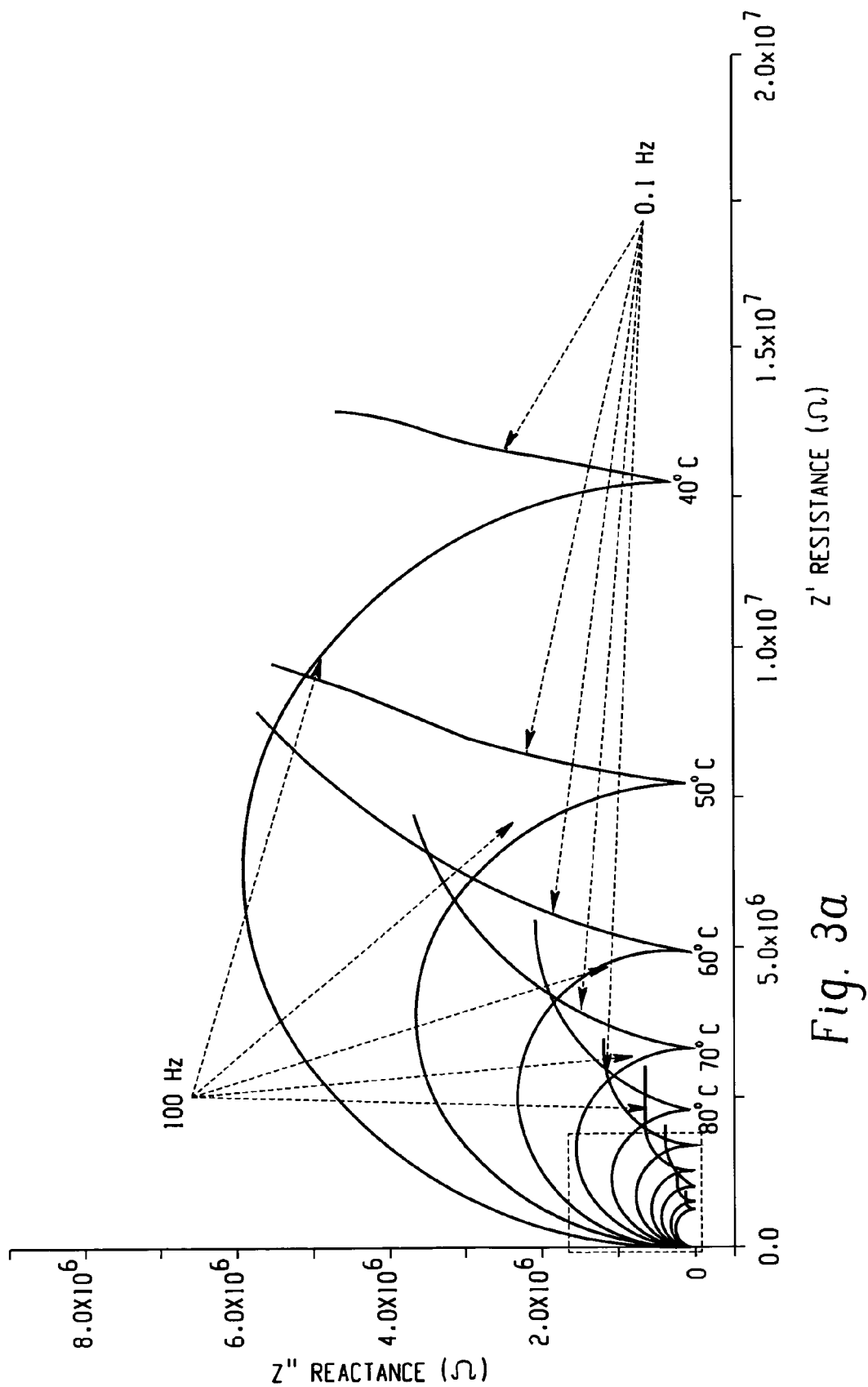
FIG. 3a is a family of Nyquist plots for engine lubricant over the temperature range 40° C.–85° C.; and, FIG. 3b is a family of Nyquist plots similar to FIG. 3a over the temperature range 85° C.–130° C.

Referring to FIG. 3a, a family of Nyquist plots are provided for a sample of internal combustion engine lubricant at various temperatures over the range 40° C. to 80° C. It will be seen from the plot that the Nyquist minimum at each temperature is clearly established, as is the behavior of the curve at the lower frequencies representative of interfacial impedance.

Figure 3B:
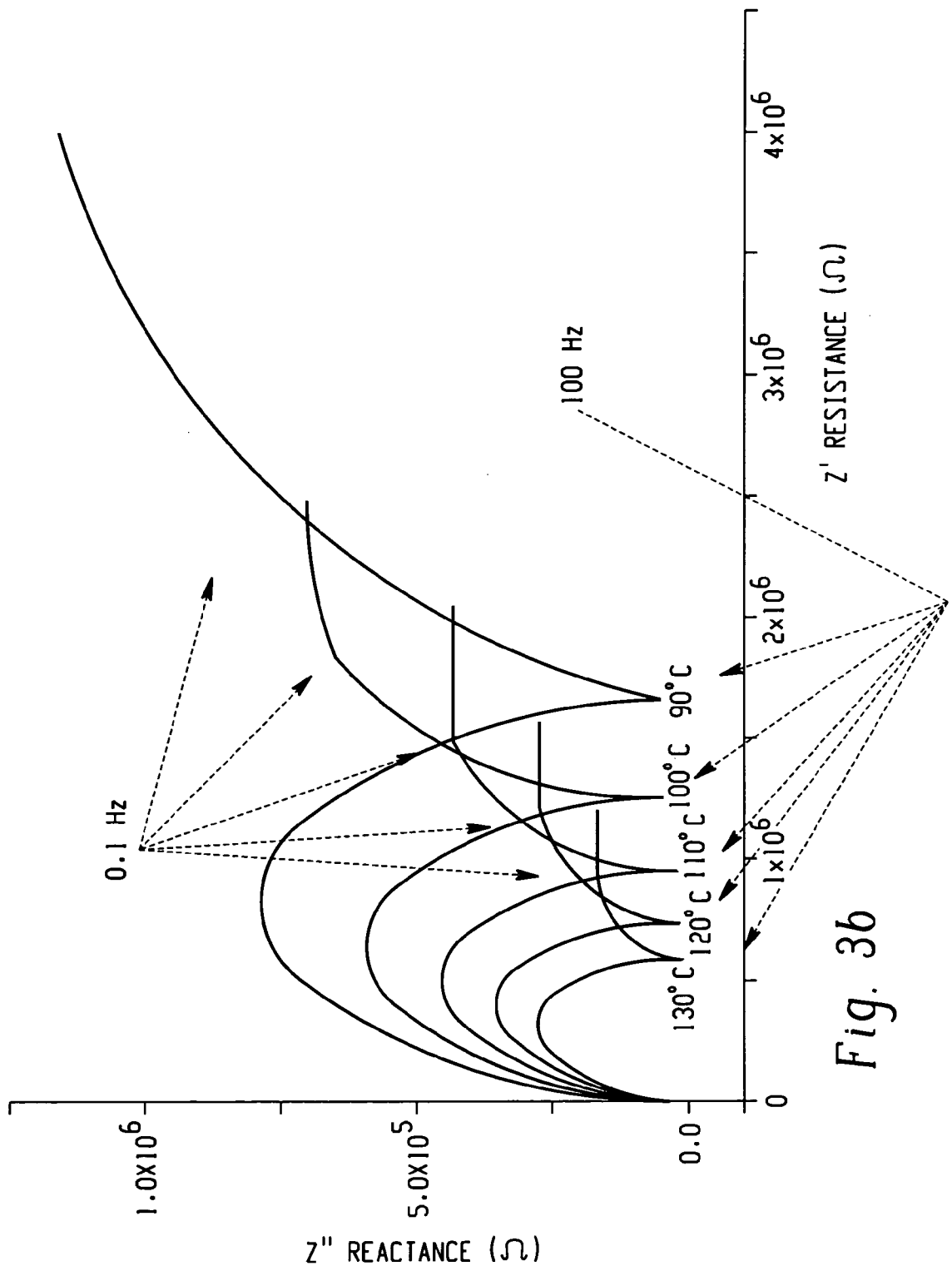

Referring to FIG. 3b, similar Nyquist plots are shown for the extended temperature range 90° C. through 130° C. where it may be seen that the Nyquist minima continue to shift but at smaller increments of resistance for each temperature. It will also be noted from FIG. 3b that the slope of the curves on the low frequency or interfacial side of the Nyquist minimum are sufficiently different from the slope at the Nyquist minimum so as to provide adequate resolution of the calculation for the angle $\Theta$.

The present invention thus provides an improved technique for employing impedance spectroscopy to determine the condition of a fluid in situ such as engine lubricant, particularly during engine operation, and provides a novel technique using the Nyquist minimum shift to compensate for changes in fluid temperature in order to enable accurate impedance measurements and determination of the fluid condition.

Although the invention has hereinabove been described with respect to the illustrated embodiments, it will be understood that the invention is capable of modification and variation and is limited only by the following claims.

What is claimed is:

1. A method of monitoring fluid condition in situ comprising:
    (a) measuring and recording the temperature $T_o$ of the fluid;
    (b) disposing electrodes in the fluid and exciting one electrode with an alternating current voltage and sweeping the frequency thereof over a certain range;
    (c) measuring the current in a second electrode and computing the reactance (Z") and resistance (Z') at a plurality of predetermined intervals of frequency in the range;
    (d) determining the frequency ($F_{Z'' \, MIN}$) in said range associated with the minimum value of reactance;
    (e) repeating steps a–d for a predetermined number of temperature intervals over a selected range of temperatures and compiling a database of values of $$F_{Z''MIN}^{T_o}$$

for each temperature interval in the range;
    (f) measuring the fluid temperature ($T_i$) and determining $$F_{Z''MIN}^{T_i}$$

by interpolation from the database;
    (g) exciting one electrode with an alternating current voltage at a frequency less than $$F_{Z''MIN}^{T_i}$$

and measuring the current in a second electrode and computing the electrode interfacial impedance $Z_S$ and computing the impedance difference ($\Delta Z = Z_S - Z_{NM}$); and,
    (h) determining the fluid condition by interpolation from a database of values of known fluid condition $\Psi$ versus $\Delta Z$.

2. The method defined in claim 1, wherein said step of sweeping the frequency in a certain range includes sweeping the frequency over the range one milliHertz to 10 kHz.

3. The method defined in claim 1, wherein said step of exciting one electrode includes applying an alternating current voltage in the range of about 0.1–2.0 volts.

4. The method defined in claim 1, wherein said step of measuring the current includes measuring magnitude and phase angle.

* * * * *

UNITED STATES PATENT AND TRADEMARK OFFICE
CERTIFICATE OF CORRECTION

PATENT NO. : 6,984,986 B2 Page 1 of 1
APPLICATION NO. : 10/786818
DATED : January 10, 2006
INVENTOR(S) : David R. Sosnowski and Gordon M. Fincannon It is certified that error appears in the above-identified patent and that said Letters Patent is hereby corrected as shown below:

Title: Insert --IN-- before SITU FLUID CONDITION MONITORING

Signed and Sealed this

Twelfth Day of September, 2006

JON W. DUDAS
*Director of the United States Patent and Trademark Office*